United States Patent
Mishima et al.

[11] Patent Number: 6,131,435
[45] Date of Patent: Oct. 17, 2000

[54] METHOD OF ESTIMATING REMAINING LIFE OF A POWER TRANSMISSION BELT

[75] Inventors: Kyoichi Mishima; Koji Kitahama, both of Hyogo, Japan

[73] Assignee: Mitsuboshi Belting Ltd., Kobe, Japan

[21] Appl. No.: 08/872,708

[22] Filed: Jun. 11, 1997

[30] Foreign Application Priority Data

Jun. 12, 1996 [JP] Japan .................................. 8-174298

[51] Int. Cl.⁷ ........................... G01N 3/56; G01N 21/88; G01N 23/00
[52] U.S. Cl. .............................. 73/7; 73/118.1; 73/119 R; 250/311; 356/237.1
[58] Field of Search ......................... 73/7, 118.1, 119 R, 73/865.9, 865.8; 356/237.1; 250/311, 216

[56] References Cited

U.S. PATENT DOCUMENTS

| | | | |
|---|---|---|---|
| 3,956,929 | 5/1976 | Jenkins, III et al. | 73/7 |
| 4,079,012 | 3/1978 | Bosniack | 508/409 |
| 4,235,091 | 11/1980 | Takano et al. | 73/7 |
| 4,237,719 | 12/1980 | Takano | 73/7 |
| 4,240,283 | 12/1980 | Takano et al. | 73/7 |
| 4,504,258 | 3/1985 | Tanaka et al. | 474/263 |
| 4,574,642 | 3/1986 | Fleischman | 73/799 |
| 4,670,309 | 6/1987 | Okada et al. | 427/387 |
| 5,351,530 | 10/1994 | Macchiarulo et al. | 73/118.1 |
| 5,413,538 | 5/1995 | Mishima | 474/263 |
| 5,462,714 | 10/1995 | Talwalker et al. | 422/37 |
| 5,753,369 | 5/1998 | Kawashima et al. | 428/396 |

FOREIGN PATENT DOCUMENTS

| | | |
|---|---|---|
| 109142 | 4/1992 | Japan . |
| 4470 | 1/1995 | Japan . |

*Primary Examiner*—Thomas P. Noland
*Attorney, Agent, or Firm*—Wood, Phillips, VanSanten, Clark & Mortimer

[57] ABSTRACT

A method for estimating remaining life of a power transmission belt. The method includes a step of providing a power transmission belt having a) a body having a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces. The method further includes the step of magnifying the one laterally spaced surface to identify cracks in the rubber at the fiber portion. Based on at least one of the nature and quantity of cracks in the rubber material, the remaining life of the power transmission belt is estimated.

21 Claims, 5 Drawing Sheets

METHOD OF ESTIMATING REMAINING LIFE OF A POWER TRANSMISSION BELT

BACKGROUND OF THE INVENTION

1. Field of the Invention

This invention relates to power transmission belts and, more particularly, to a method of estimating the remaining life of a power transmission belt.

2. Background Art

It is common for automobile makers to collect and investigate data pertaining to the life of power transmission belts on engines subjected to road running tests to estimate the remaining life thereof. It is desirable to be able to make a reasonable estimate of remaining life after a relatively short running distance.

This type of power transmission belt is commonly made with a rubber body having short fibers embedded therein. The fibers project laterally between spaced, pulley-engaging side surfaces to increase lateral pressure resistance and reduce rubber wear. The fibers have exposed portions at the side surfaces. Exemplary of such a belt is that shown in Japanese Provisional Patent Publication No. 7-4470, assigned to the assignee herein.

Figures 2, 4:
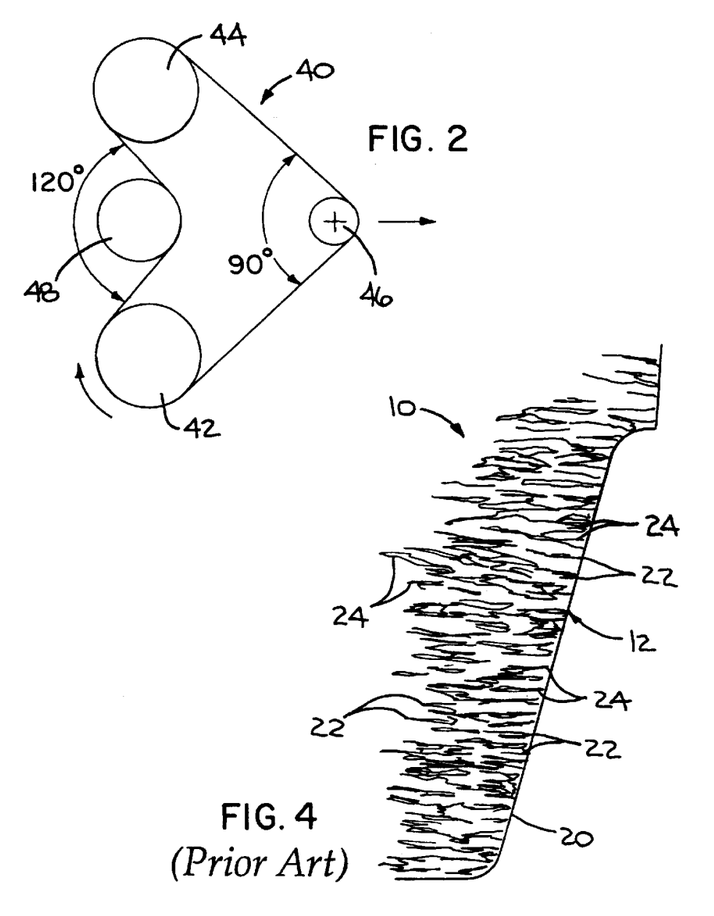
FIG. 2 is a schematic representation of a dynamic testing device for a power transmission belt.
FIG. 4 is a fragmentary, perspective view of a V-ribbed belt of the type with which the present method can be practiced.
Figure 5:
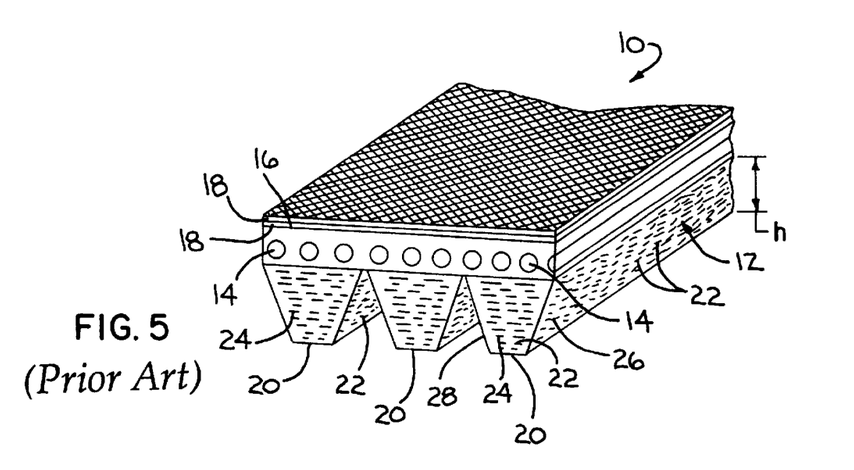
FIG. 5 is an enlarged, fragmentary, cross-sectional view of a rib on the belt in FIG. 4.

In FIGS. 4 and 5, a V-ribbed belt, as in Japanese Provisional Patent Publication No. 7-4470, is shown at 10. The belt 10 has a body 12 with load carrying cords 14 embedded therein and extending lengthwise of the belt 10. The belt body 12 has an outer surface 16 to which two layers 18 of canvas are adhered. A plurality of, and in this case three, V-shaped ribs 20 are provided on the inside of the belt body 12. The ribs 20 are spaced laterally from each other and extend in a lengthwise direction. The ribs 20 are made from rubber within which short, reinforcing aramid fibers 22 are embedded. The ribs 20 also have embedded therein short, non-aramid, reinforcing fibers 24 which have a wear resistance that is less than that of the aramid fibers 22. The fibers 22, 24 have lengths oriented generally in a lateral direction. The fibers 22, 24 project from 0.1 to 3.0 mm from oppositely facing rib surfaces 26, 28, which surfaces 26, 28 engage complementary surfaces on a cooperating pulley (not shown).

With the belt 10 trained around a cooperating pulley, the projecting portions of the aramid fibers 22 are bent by the pulley against the rib surfaces 26, 28. This reduces wear on the rubber in the ribs 20 by the pulley during use. Further, the projecting portions of the fibers 22 reduce the coefficient of friction between the rubber in the ribs 20 and the cooperating pulley, thereby reducing noise generation resulting from the ribs 20 momentarily sticking on the pulley.

The non-aramid fibers 24 prevent the bent aramid fibers 22 from pressing into the rubber defining the surfaces 26, 28. The aramid fibers 22 thus remain between the rubber in the ribs 20 and cooperating pulleys. If the bent fibers 22 were allowed to embed in the rubber defining the surfaces 26, 28, the sides of these fibers 22 would be exposed, thereby making slippage between the belt 10 and cooperating pulley more likely.

By reason of having the aramid fibers bent without being embedded in the surfaces 26, 28, the belt 10 is allowed to seat more deeply into cooperating pulley grooves, which thereby reduces belt tension, as at initial system set up. After the belt 10 is run for a period of time, the aramid fibers 22 bent by the pulleys against the exposed non-aramid fibers 24 are pinched and eventually severed.

The aramid fibers 22 wear away, as shown in FIG. 5, at roughly the time that the tension of the belt, which reduces as the belt operates, has stabilized. Once the fibers 22 wear away, the coefficient of friction between the belt 10 and cooperating pulleys increases, thereby improving power transmission performance.

To estimate the remaining life of the above power transmission belt 10 using conventional techniques, the surfaces 26, 28 are visually observed. The abnormal conditions of the belt are divided into five different evaluation categories, identified as A–E, as in Table 1, below.

TABLE 1

| Evaluation Category | Result of visual observation | Coefficient of remaining life |
| --- | --- | --- |
| A | No abnormality observed. | 1 or more |
| B | Cracks about one half the height of rubber transmission section observed. | one half |
| C | Cracks over the height of rubber transmission section observed. | one quarter |
| D | Rubber transmission section broken. | zero |
| E | Rubber transmission section severed. | zero |

A coefficient of the remaining life is determined by dividing the travelling distance until the belt life expires after a particular observation point by the running distance up to the observation point, hereinafter referred to as the "actual running distance".

It is difficult to make meaningful estimations of remaining life when the actual running distance is only a short distance. For example, there are many evaluations which will fall into category A where no abnormality is identifiable by an unmagnified, visual observation. As a result, the coefficient of the remaining life would be estimated as 1 or more, although there is actually a considerable difference in the remaining life.

As an alternative to mere visual observation, it is know to measure the hardness of the rubber in the belt. However, this estimation varies greatly depending upon operating conditions.

SUMMARY OF THE INVENTION

In one form of the invention, a method is provided for estimating remaining life of a power transmission belt. The method includes the step of providing a power transmission belt having a) a body having a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces. The method further includes the step of magnifying the one laterally spaced surface to identify cracks in the rubber at the fiber portion. Based on at least one of the nature and quantity of cracks in the rubber material, the remaining life of the power transmission belt is estimated.

The remaining life may be estimated based on the number of cracks in the rubber material at the fiber portions and/or based on the number of cracks in the rubber material spanning between the fiber portions.

Cracks which are invisible to the naked eye develop and grow around the exposed portions of the fibers with the passage of time. As the cracks grow in number and extent, the remaining belt life decreases.

A coefficient of one or more, which decreases with the number of cracks in the rubber material at the fiber portions and the number of cracks in the rubber material spanning between the fiber portions, may be assigned and multiplied by the actual running distance to estimate the remaining life.

Five different coefficients, each indicative of a different abnormal condition for the power transmission belt, may be assigned.

The abnormality to which the coefficient is assigned may be at least one of an abnormality in the fibers or an abnormality in the rubber material in which the fibers are embedded.

In one form, a first coefficient is assigned that is indicative of irregularities in the short fibers, a second coefficient is assigned indicative of cracks in the rubber material around some of the fiber portions, a third coefficient is assigned indicative of cracks in the rubber material around all of the fiber portions or cracks in the rubber material around only some of the fiber portions and spanning between the fiber portions, a fourth coefficient is assigned indicative of cracks in the rubber material around substantially all of the fiber portions with only some cracks in the rubber material spanning between the fiber portions, and a fifth coefficient is assigned indicative of all cracks in the rubber material spanning between the fiber portions.

The coefficients may increase from the fifth coefficient to the first coefficient.

The coefficient may be assigned so that a first coefficient is indicative of cracks in the rubber material around the fiber portions and a second coefficient is indicative of cracks in the rubber material spanning between the fiber portions, with the first coefficient being greater than the second coefficient.

The coefficients may be assigned values between 1 and 2.

Magnifying may be carried out as through a microscope, an electron microscope, or a magnifying glass.

The invention also contemplates a method of estimating the remaining life of a power transmission belt, which method includes the steps of providing a power transmission belt having a) a body made of a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces. The method may include the step of magnifying one laterally spaced surface to identify a condition that is not observable without magnification. Based on the condition that is not observable without magnification, the remaining life of the power transmission belt may be estimated.

The step of estimating the remaining life of the power transmission belt may include the step of assigning coefficients indicative of at least one of cracks in the rubber material and irregularities in the fibers and multiplying actual running distance for the power transmission belt by the coefficient to estimate the remaining life.

The coefficients may be predetermined based on actual belt operations.

The invention allows the remaining life of a power transmission belt to be meaningfully estimated through a simple process. The estimation can be made after a relatively short running distance, even though abnormality is not detectable by the naked eye. Several different criteria can be used to make this analysis.

DETAILED DESCRIPTION OF THE DRAWINGS

The power transmission belt 10, previously described, is but exemplary of the different types of belts with which the inventive method can be practiced. The invention can be practiced with virtually any type of power transmission belt in which one or more ribs fit into complementary grooves on a cooperating pulley and in which short reinforcing fibers are embedded for lateral stability and exposed at pulley-engaging side surfaces on the belt rib(s).

According to the invention, the remaining life of the power transmission belt 10 is estimated using evaluation different subcategories of abnormality, as identified by A-1, A-2, A-3, A-4, and A-5 in FIG. 1 and in Table 2, below. The remaining belt life is the running distance from the actual running distance to the point that the state of evaluation category D (Table 1) is reached, i.e. the remaining life reduces to zero. The abnormalities in A-1 through A-5 are not detectable by visual observation using the naked eye. Each abnormality is observable such as by use of an electron microscope, a microscope, or a magnifying glass. The different subcategories relate to the nature and degree of cracking in rubber material at one of the exemplary belt surfaces 26, 28.

Cracks which are invisible to the naked eye generally first develop around the fibers 22, 24, with the number increasing over time. Progressive crack development through continued use causes the cracks to "span" between fibers 22, 24.

It should be initially noted, as will be demonstrated using the various photomicrographs in FIGS. 6 to 10 herein, that the aramid and non-aramid fibers 22, 24, respectively, vary in diameter. For purposes of explanation with respect to FIG. 1, the diameter of the fibers 22, 24 will be depicted as the same.

In FIG. 1, K identifies generically cracks in the rubber material defining the surfaces 26, 28. $K_1$ identifies cracks observed around exposed portions 30 of the fibers 22, 24, with $K_2$ identifying cracks spanning between the exposed portions 30 of the fibers 22, 24.

Figures 1A, 1B, 1C, 1D, 1E:
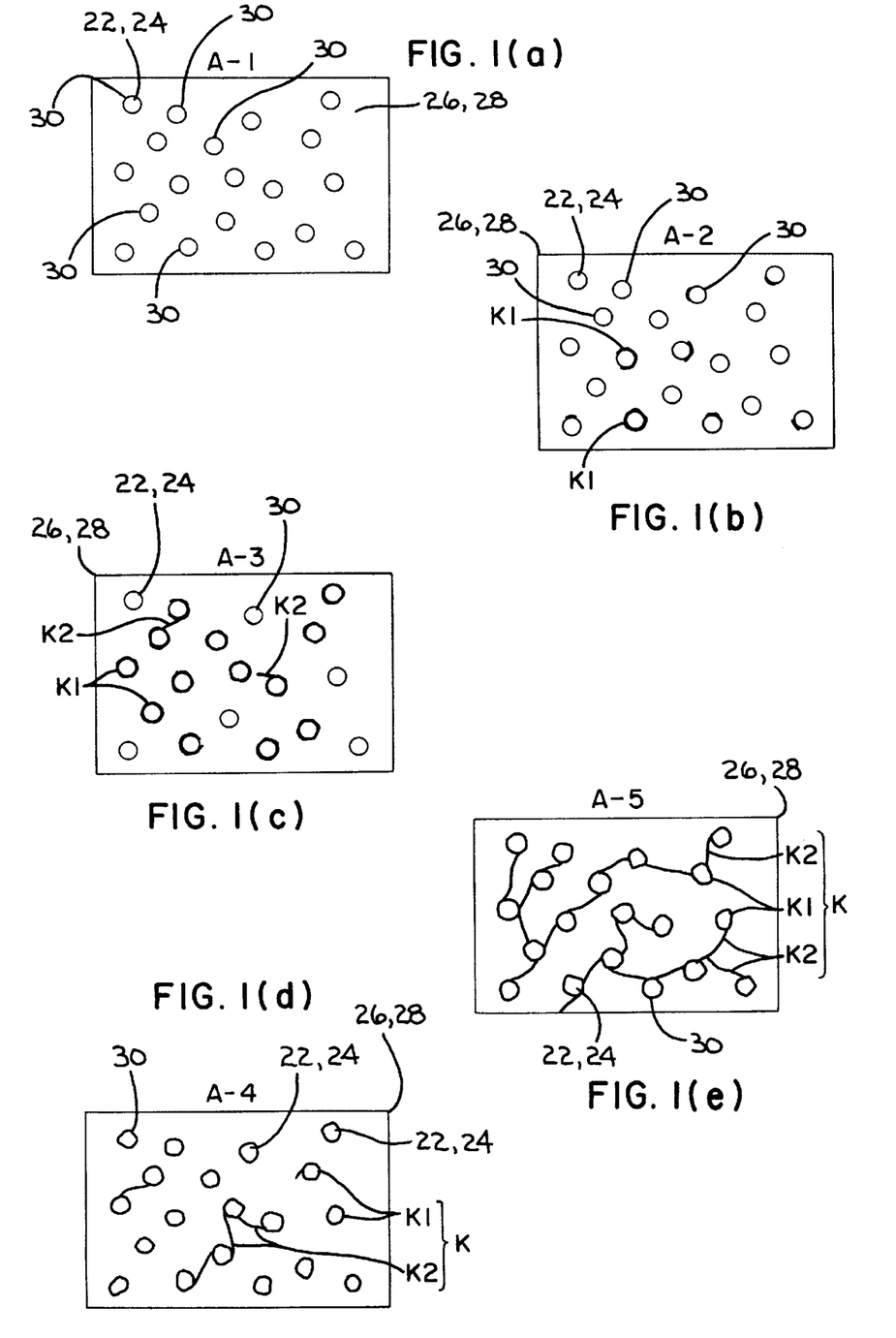
FIG. 1 shows five different schematic representations of conditions observable under magnification and used to estimate the remaining life of a power transmission belt, according to the present invention.

Subcategory A-1, as depicted in FIG. 1(a), is a condition in which the projecting portions of the aramid fibers 22 are still intact and no rubber irregularities are observed. Irregularities in the projecting portions of the aramid fibers 22 are observed. Subcategory A-2, as depicted in FIG. 1(b), is a condition in which the projecting portions of the aramid fibers 22 have been severed and cracks $K_1$ are observed around some of the fibers 22, 24. Subcategory A-3, as depicted in FIG. 1(c), is a condition in which cracks $K_1$ are observed around substantially all of the fibers 22, 24 or cracks are observed around substantially less than all of the exposed fiber portions 30 but these cracks span between the fiber portions 30 to form bridging cracks $K_2$. Subcategory A-4, as depicted in FIG. 1(d), is a condition in which cracks are observed around almost all of the exposed fiber portions 30 and bridging portions $K_2$ are partly formed therein. Subcategory A-5, as depicted in FIG. 1(e), is a condition in which the cracks $K_2$ span between almost all of the short fibers.

When a large number of belt samples 10 are subjected to a road running test, or a simulation test equivalent thereto, and the evaluation categories and divided into the above-described subcategories A-1, A-2, A-3, A-4, A-5 and the categories B, C, D and E, the average values of the actual running distances of the samples in each of the categories/subcategories are taken as $a_1$, $a_2$, $a_3$, $a_4$ and $a_5$ and b, c, d and e. The evaluation subcategory D shows a condition in which the rubber material is broken and a condition in which the belt life has already expired. Thus, the value obtained by subtracting $a_1$, $a_2$, $a_3$, $a_4$, $a_5$ and b, c from the running distance d leading to the evaluation category D will give the remaining life $\eta$.

Thus, if the remaining lives of the power transmission belts divided into the evaluation subcategories A-1, A-2, A-3, A-4, and A-5 are taken as $\eta_1$, $\eta_2$, $\eta_3$, $\eta_4$, and $\eta_5$, they are determined as follows:

$\eta_1 = d - a_1$ $\eta_2 = d - a_2$ $\eta_3 = d - a_3$ $\eta_4 = d - a_4$ $\eta_5 = d - a_5$ Next, the coefficients for the remaining life of the belt 10 are estimated from the ratios of the above remaining lives to the actual running distances. If the ratios are taken as $\kappa_1$, $\kappa_2$, $\kappa_3$, $\kappa_4$, and $\kappa_5$, respectively, they are determined as follows:

$\kappa_1 = \eta_1/a_1 = (d/a_1) - 1$ $\kappa_2 = \eta_2/a_2 = (d/a_2) - 1$ $\kappa_3 = \eta_3/a_3 = (d/a_3) - 1$ $\kappa_4 = \eta_4/a_4 = (d/a_4) - 1$ $\kappa_5 = \eta_5/a_5 = (d/a_5) - 1$ It is known that the power transmission belt of evaluation category A has a remaining life of at least equal to the present running distance or more and the coefficient for the remaining life becomes 1 or more.

If the above-described coefficients for remaining life are obtained in advance for each type of power transmission belt, the remaining lives $\eta_1$, $\eta_2$, $\eta_3$, $\eta_4$, and $\eta_5$ could be estimated by multiplying the actual running distances $a_1$, $a_2$, $a_3$, $a_4$ and $a_5$ by the aforementioned coefficients of remaining life $\kappa_1$, $\kappa_2$, $\kappa_3$, $\kappa_4$, and $\kappa_5$.

It is also possible to further divide a) the evaluation subcategory A-1 using proportions of abnormalities observed, b) the evaluation subcategory A-2 by proportions of cracks $K_1$ around the short fibers, and c) the evaluation of subcategories A-3 to A-5 by a combination of proportions of cracks $K_1$ around the short fibers and proportions of spanning portions $K_2$ between the short fibers.

EXAMPLE

The power transmission belt 10 was used to obtain the coefficients of remaining life $\kappa_1$, $\kappa_2$, $\kappa_3$, $\kappa_4$, and $\kappa_5$ through experimentation. The rubber material in the belt body was made of 5 parts by weight of aramid short fiber and 13 parts by weight of nylon short fibers per 100 parts by weight of chloroprene rubber. The length of the aramid short fibers and the non-aramid short fibers was 2 to 10 mm. The belt had a V-shaped rib with a circumferential length of 1100 mm.

In FIG. 2, a dynamic testing device is shown at 40 for the power transmission belts. The testing device 40 has a driving pulley 42 with a diameter of 120 mm that is rotated at a speed of 4900 rpm, a driven pulley 44 having a diameter of 120 mm and a load of 12 P.S., a stationary pulley 46 having a diameter of 45 mm and loaded with an initial load of 57 kgf, and an idler pulley 48 having a diameter of 85 mm. The system was run at an ambient temperature of 85° C.

The belt 10 was trained around the pulleys 42, 44, 46, 48 and operated. The operation was interrupted at predetermined intervals to determine the amount of crack development to produce data for evaluation purposes. The results are shown in FIG. 3.

In the test device 40, with the drive pulley 42 rotated at a constant speed, the running distance is proportional to the operating time. For purposes herein, the running distance will be expressed in terms of a "running time".

Figure 3:
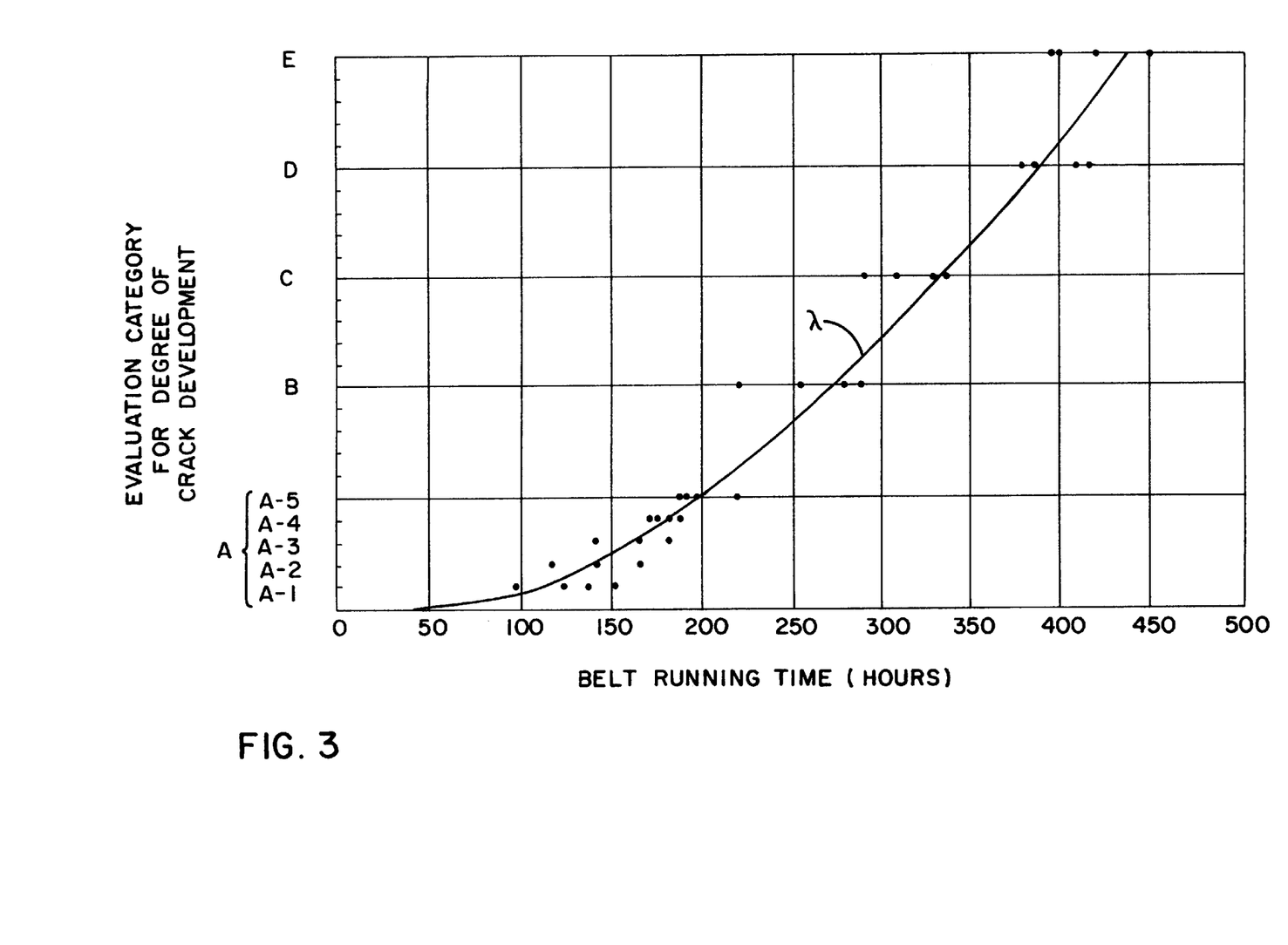
FIG. 3 is a graph showing the results of a dynamic test for the inventive power transmission belt.

Referring to FIG. 3, the relationship between the running time and the degree of crack development is identified by black spots, with the approximate average of the data represented by a curve $\lambda$. The average values of the present running time by the evaluation classes were $a_1$=128 hours, $a_2$=142 hours, $a_3$=170 hours, $a_4$=180 hours, $a_5$=200 hours, b=262 hours, c=318 hours, d=399 hours, and e=418 hours.

Data accumulated through a road running test was added to these experimental results to set the coefficients of remaining life to $\kappa_1$=2.00, $\kappa_2$=1.75, $\kappa_3$=1.50, $\kappa_4$=1.25, and $\kappa_5$=1.00. The relationships therebetween are summarized in Table 2, below.

TABLE 2

| Evaluation Subcategory | Results of Visual Observation Under Magnification | Coefficient of Remaining Life |
| --- | --- | --- |
| A-1 | Abnormalities of short fibers observed. | 2.00 |
| A-2 | Irregularities of short fibers eliminated, and cracks observed around short fibers. | 1.75 |
| A-3 | Cracks observed around almost all of short fibers, or a few cracks observed but the cracks span between short fibers. | 1.50 |
| A-4 | Cracks observed around almost all of short fibers, and some of cracks between short fibers are spanning. | 1.25 |
| A-5 | Almost all of cracks are spanning between short fibers. | 1.00 |

After determining the coefficients of remaining life through experimentation for the power transmission belt, the remaining life can be estimated from the state of crack development which is not visually observable through the naked eye.

Figure 6:
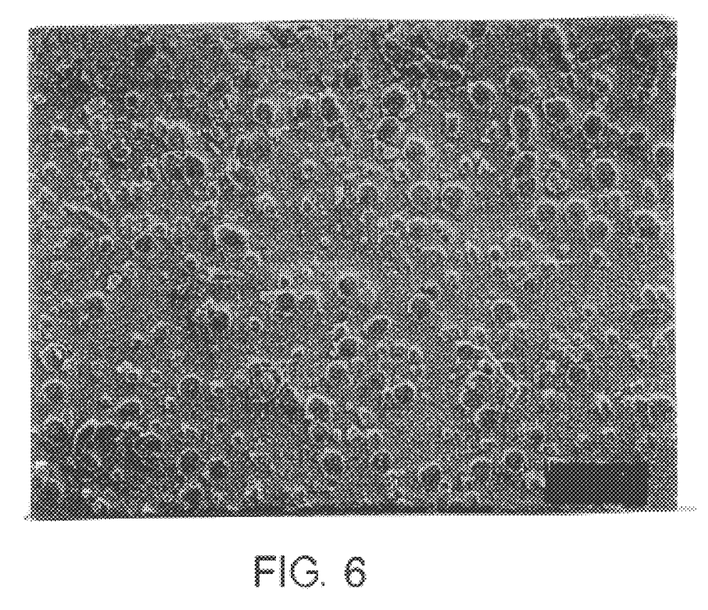
FIG. 6 is a photomicrograph of a surface of a power transmission belt showing a first condition used to estimate the remaining life of a power transmission belt, according to the present invention.
Figure 7:
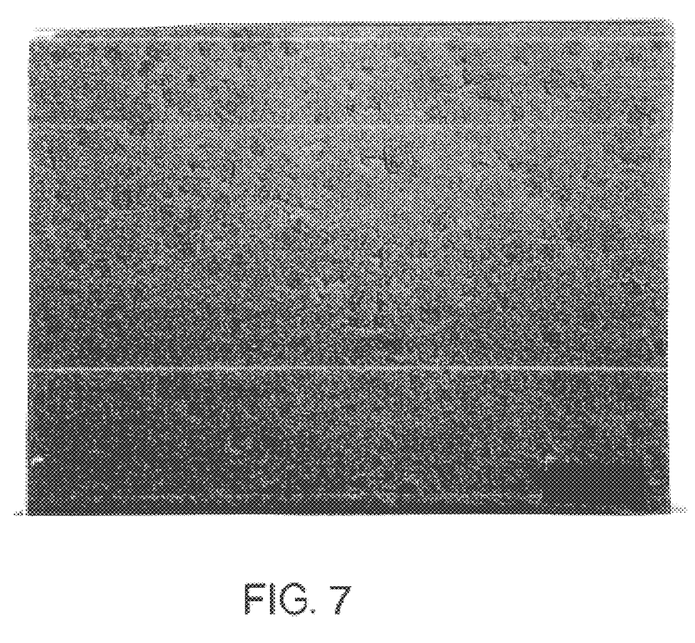
FIG. 7 is a photomicrograph of a surface of a power transmission belt showing a second condition used to estimate the remaining life of a power transmission belt, according to the present invention.
Figure 8:
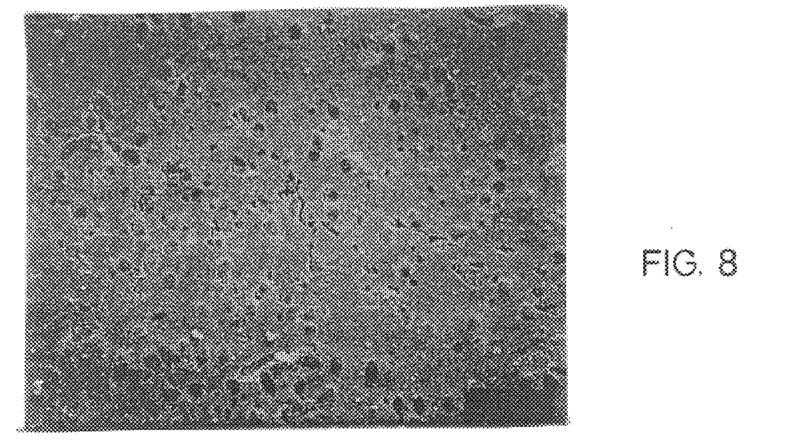
FIG. 8 is a photomicrograph of a surface of a power transmission belt showing a third condition used to estimate the remaining life of a power transmission belt, according to the present invention.
Figure 9:
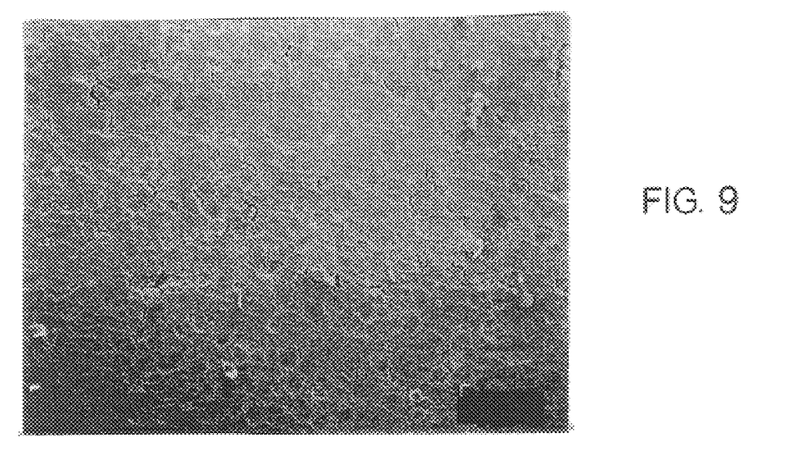
FIG. 9 is a photomicrograph of a surface of a power transmission belt showing a fourth condition used to estimate the remaining life of a power transmission belt, according to the present invention.
Figure 10:
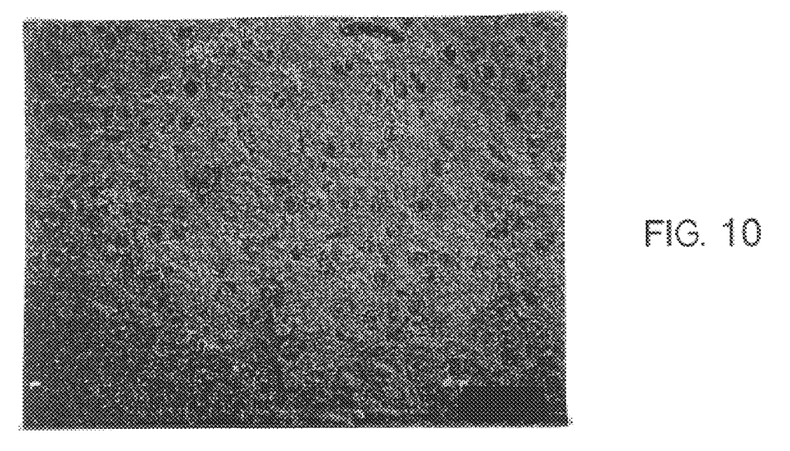
FIG. 10 is a photomicrograph of a surface of a power transmission belt showing a fifth condition used to estimate the remaining life of a power transmission belt, according to the present invention.

Samples of photomicrographs of evaluation subcategories taken from the side surface 26 of the power transmission belt 10 are shown in FIGS. 6–10. FIG. 6 is a photomicrograph corresponding to the condition in subcategory A-1. FIG. 6 is a photomicrograph corresponding to the condition in subcategory A-2. FIG. 7 is a photomicrograph corresponding to the condition in subcategory A-3. FIG. 8 is photomicrograph corresponding to the condition in subcategory A-4. FIG. 9 is a photomicrograph corresponding to the condition in subcategory A-5.

In the photomicrographs, of the short fibers which are circular in cross section, the thicker ones are non-aramid short fibers, with the thinner ones being the aramid short fibers. Black and thin portions are cracks, with the cracks tending to form more readily around the non-aramid short fibers.

With the invention, the remaining life of the belt can be predicted with meaningful accuracy even though the belt surfaces appear to be perfect to the naked eye. The data analysis is accumulated under magnification. This allows prediction of life expectancy after a relatively short running time as in a road running test. By predetermining the correspondence between the categorized abnormalities and the remaining belt life in advance through experimentation, coefficients can be predetermined and used to estimate remaining belt life for belts having a similar construction to those pre-run. Meaningful numerical life expectancies can thus be established using the present invention.

The foregoing disclosure of specific embodiments is intended to be illustrative of the broad concepts comprehended by the invention.

We claim:

1. A method of estimating remaining life of a power transmission belt, said method comprising the steps of:
   providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;
   magnifying the one laterally spaced surface to identify certain cracks in the rubber material with at least one of the nature and quantity of the certain cracks being undetectable to the naked eye without magnification; and
   based on at least one of the nature and quantity of the certain cracks in the rubber material identified through magnification, estimating the remaining life of the power transmission belt.

2. The method of estimating remaining life of a power transmission belt according to claim 1 wherein the step of estimating the remaining life comprises the step of estimating the remaining life based on the number of cracks in the rubber material at the fiber portions.

3. The method of estimating remaining life of a power transmission belt according to claim 1 wherein the step of estimating the remaining life comprises the step of estimating the remaining life based on the number of cracks in the rubber material spanning between the fiber portions.

4. The method of estimating remaining life of a power transmission belt according to claim 1 wherein the step of estimating the remaining life comprises the step of estimating the remaining life based on the number of cracks at the fiber portions and the number of cracks spanning between the fiber portions.

5. The method of estimating remaining life of a power transmission belt according to claim 1 including the step of assigning a coefficient based upon an abnormality identified under magnification of at least one of the fibers and the rubber material in which the fibers are embedded and multiplying actual running distance for the power transmission belt by the coefficient to estimate the remaining life.

6. The method of estimating remaining life of a power transmission belt according to claim 1 wherein the step of magnifying comprises the step of magnifying using one of a microscope, an electron microscope, and a magnifying glass.

7. A method of estimating remaining life of a power transmission belt, said method comprising the steps of:
   providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;
   magnifying the one laterally spaced surface to identify cracks in the rubber material;
   based on at least one of the nature and quantity of cracks in the rubber material estimating the remaining life of the power transmission belt,
   wherein the step of estimating the remaining life comprises the step of estimating the remaining life based on the number of cracks at the fiber portions and the number of cracks spanning between the fiber portions;
   assigning a coefficient of one or more which decreases with the number of cracks on the rubber material at the fiber portions and the number of cracks in the rubber material spanning between the fiber portions; and
   multiplying actual running distance for the power transmission belt by the coefficient to estimate the remaining life.

8. The method of estimating remaining life of a power transmission belt according to claim 7 wherein the step of assigning a coefficient comprises the steps of assigning at least five different coefficients each indicative of a different abnormal condition for the power transmission belt.

9. A method of estimating remaining life of a power transmission belt, said method comprising the steps of:
   providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;
   magnifying the one laterally spaced surface to identify cracks in the rubber material;
   based on at least one of the nature and quantity of cracks in the rubber material estimating the remaining life of the sower transmission belt;
   assigning a coefficient based upon an abnormality identified under magnification of at least one of the fibers and the rubber material in which the fibers are embedded; and
   multiplying actual running distance for the power transmission belt by the coefficient to estimate the remaining life, wherein the step of assigning a coefficient comprises the step of assigning a) a first coefficient indicative of irregularities in the short fibers, b) a second coefficient indicative of cracks in the rubber material around some of the fiber portions, c) a third coefficient indicative of cracks in the rubber material around all of the fiber portions or cracks in the rubber material around only some of the fiber portions and spanning between fiber portions, d) a fourth coefficient indicative of cracks in the rubber material around substantially all fiber portions with only some cracks in the rubber material spanning between fiber portions and e) a fifth coefficient indicative of all cracks in the rubber material spanning between fiber portions.

10. The method of estimating remaining life of a power transmission belt according to claim 9 wherein the coefficient increases from the fifth coefficient to the first coefficient.

11. A method of estimating remaining life of a power transmission belt, said method comprising the steps of:

providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;

magnifying the one laterally spaced surface to identify cracks in the rubber material;

based on at least one of the nature and quantity of cracks in the rubber material estimating the remaining life of the power transmission belt;

assigning a coefficient based upon an abnormality identified under magnification of at least one of the fibers and the rubber material in which the fibers are embedded; and multiplying actual running distance for the powertransmission belt by the coefficient to estimate the remaining life, wherein the step of assigning a coefficient comprises the step of assigning a first coefficient indicative of cracks in the rubber material around the fiber portions and a second coefficient indicative of cracks in the rubber material spanning between the fiber portions and the first coefficient is greater than the second coefficient.

12. A method of estimating remaining life of a power transmission belt, said method comprising the steps of:

providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;

magnifying the one laterally spaced surface to identify cracks in the rubber material;

based on at least one of the nature and quantity of cracks in the rubber material estimating the remaining life of the power transmission belt;

assigning a coefficient based upon an abnormality identified under magnification of at least one of the fibers and the rubber material in which the fibers are embedded, wherein the step of assigning a coefficient comprises the step of assigning a) a first coefficient indicative of irregularities in the short fibers, b) a second coefficient indicative of cracks in the rubber material around some of the fiber portions, c) a third coefficient indicative of cracks in the rubber material around all of the fiber portions or cracks in the rubber material around only some of the fiber portions and spanning between fiber portions, d) a fourth coefficient indicative of cracks in the rubber material spanning between fiber portions and e) a fifth coefficient indicative of all cracks in the rubber material spanning between fiber portions; and multiplying actual running distance for the powertransmission belt by the coefficient to estimate the remaining life, wherein the step of assigning a coefficient comprises the step of assigning coefficients of between 1 and 2 for each of the first through fifth coefficients.

13. A method of estimating remaining life of a power transmission belt, said method comprising the steps of:

providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;

magnifying the one laterally spaced surfaces to identify a condition that is not observable without magnification; and based on the condition that is not observable without magnification, estimating the remaining life of the power transmission belt.

14. The method of estimating remaining life of a power transmission belt according to claim 13 wherein the step of estimating the remaining life of the power transmission belt comprises the steps of assigning coefficients indicative of at least one of cracks in the rubber material and irregularities of the fibers and multiplying actual running distance for the power transmission belt by the coefficient to estimate the remaining life.

15. The method of estimating remaining life of a power transmission belt according to claim 14 wherein the step of assigning a coefficient comprises the steps of assigning at least five different coefficients each indicative of a different abnormal condition for the power transmission belt.

16. The method of estimating remaining life of a power transmission belt according to claim 14 wherein the step of magnifying comprises the step of magnifying using at least one of a microscope, an electron microscope, and a magnifying glass.

17. The method of estimating remaining life of a power transmission belt according to claim 14 including the step of predetermining the coefficients based on actual belt operation and the step of assigning coefficients comprises the step of assigning coefficients derived from the actual belt operation.

18. A method of estimating remaining life of a power transmission belt, said method comprising the steps of:

providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;

magnifying the one laterally spaced surface to identify a condition that is not observable without magnification; and based on the condition that is not observable without magnification, estimating the remaining life of the power transmission belt, wherein the step of estimating the remaining life of the power transmission belt comprises the steps of assigning coefficients indicative of at least one of cracks in the rubber material and irregularities of the fibers and multiplying actual running distance for the power transmission belt by the coefficient to estimate the remaining life, wherein the step of assigning a coefficient comprises the step of assigning a) a first coefficient indicative of irregularities of short fibers, b) a second coefficient indicative of cracks in the rubber material around some of the fiber portions, c) a third coefficient indicative of cracks in the rubber material around all of the fiber portions or cracks in the rubber material around only some of the fiber portions and spanning between fiber portions, d) a fourth coefficient indicative of cracks in the rubber material around substantially all fiber portions with only some cracks in the rubber material spanning between fiber portions and e) a fifth coefficient indicative of all cracks in the rubber material spanning between fiber portions.

19. The method of estimating remaining life of a power transmission belt according to claim 18 wherein the coefficient increase from the fifth coefficient to the first coefficient.

20. A method of estimating remaining life of a power transmission belt, said method comprising the steps of:

providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;

magnifying the one laterally spaced surface to identify a condition that is not observable without magnification; and based on the condition that is not observable without magnification, estimating the remaining life of the power transmission belt, wherein the steps of estimating the remaining life of the power transmission belt comprises the steps of assigning coefficients indicative of at least one of cracks in the rubber material and irregularities of the fibers and multiplying actual running distance for the power transmission belt by the coefficient to estimate the remaining life, wherein the step of assigning a coefficient comprises the step of assigning a first coefficient indicative of cracks in the rubber material around the fiber portions and a second coefficient indicative of cracks in the rubber material spanning between the fiber portions and the first coefficient is greater than the second coefficient.

21. A method of estimating remaining life of a power transmission belt, said method comprising the steps of:

providing a power transmission belt having a) a body comprising a rubber material with a length and laterally spaced surfaces to engage a cooperating pulley and b) a plurality of fibers embedded in the rubber material and projecting in a lateral direction so that a plurality of the fibers have a portion that is exposed at one of the laterally spaced surfaces;

magnifying the one laterally spaced surface to identify a condition that is not observable without magnification; and based on the condition that is not observable without magnification, estimating the remaining life of the power transmission belt, wherein the steps of estimating the remaining life of the power transmission belt comprises the steps of assigning coefficients indicative of at least one of cracks in the rubber material and irregularities of the fibers and multiplying actual running distance for the power transmission belt by the coefficient to estimate the remaining life, wherein the step of assigning a coefficient comprises the steps of assigning at least five different coefficients each indicative of a different abnormal condition for the power transmission belt, wherein the step of assigning a coefficient comprises the step of assigning coefficients of between 1 and 2 for each of the first through fifth coefficients.

* * * * *